United States Patent [19]

White

[11] Patent Number: 4,886,488
[45] Date of Patent: Dec. 12, 1989

[54] GLAUCOMA DRAINAGE THE LACRIMAL SYSTEM AND METHOD

[76] Inventor: Thomas C. White, 1127 Holly Dr., Sioux Falls, S. Dak. 57105

[21] Appl. No.: 229,746

[22] Filed: Aug. 4, 1988

Related U.S. Application Data

[63] Continuation of Ser. No. 82,837, Aug. 6, 1987, abandoned.

[51] Int. Cl.⁴ .............................................. A61M 1/00
[52] U.S. Cl. ........................................ 604/9; 604/294
[58] Field of Search ................................. 604/9, 294

[56] References Cited

U.S. PATENT DOCUMENTS

| | | | |
|---|---|---|---|
| 3,726,284 | 4/1973 | Parker | 128/350 |
| 3,788,327 | 1/1974 | Donowitz et al. | 604/9 |
| 3,949,750 | 4/1976 | Freeman | 604/294 |
| 4,037,604 | 7/1977 | Newkirk | 604/9 |
| 4,225,979 | 10/1980 | Rey et al. | 604/9 |
| 4,402,681 | 9/1983 | Haas et al. | 604/9 |
| 4,604,087 | 8/1986 | Joseph | 604/9 |

OTHER PUBLICATIONS

Mascati, "A New Surgical Approach for the Control of a Class of Glaucoma", International Surgery, vol. 47, No. 1, pp. 10-15, (Jan. 1967).
Advertisement Published in the Jan., 1975 issue of Archives of Ophthalmology.

Primary Examiner—Albert W. Davis Jr.
Attorney, Agent, or Firm—Mary P. Bauman; Gregory P. Kaihoi; James R. Haller

[57] ABSTRACT

A device and method for allowing fluid to flow from the interior of the eye into the nasolacrimal drainage system associated with the eye to relieve high intraocular pressure in the treatment of glaucoma. The method employs a flexible tube having one end extendable into the anterior chamber of the eye and having its other end in communication with the nasolacrimal drainage system of the eye. A one-way valve is provided within the tube to restrain liquid flow to a direction from the anterior chamber of the eye toward the lacrimal drainage system. The method includes the steps of inserting one end of the tube into the anterior chamber of the eye and inserting the other end of the tube into a portion of the nasolacrimal drainage system; aqueous humor is permitted to escape into the tube at the anterior chamber end, and flows outwardly into the passages of the nasolacrimal system. One or more one-way valve within the tube permit fluid flow only away from the anterior chamber.

9 Claims, 2 Drawing Sheets

GLAUCOMA DRAINAGE THE LACRIMAL SYSTEM AND METHOD

This application is a continuation of application Ser. No. 082,837, filed Aug. 6, 1987, now abandoned.

FIELD OF THE INVENTION

This invention relates to the field of ophthalmology, and particularly to devices and methods for conducting fluids within and about the eye and the lacrimal drainage system.

BACKGROUND OF THE INVENTION

Glaucoma is a disease characterized by elevated intraocular pressure which, if not checked, may lead to nerve damage and visual loss. Pressures in the range of from about 15±3 mm Hg up to about 21 mm Hg may be considered to be in the normal range for human beings, whereas pressures substantially above that range are considered abnormally high. If pressures in the higher range are maintained for substantial periods of time, damage to the optica nerve of the eye may occur, leading to a narrowing of the field of vision and eventually to blindness if not appropriately treated. Although in certain cases glaucoma can be treated through the aministration of certain medicines such as pilocarpine, epinephrine and timololmaleate, it is often necessary to surgically provide for the release of intraocular pressure for those patients who do not respond to drug therapy or who continue to lose vision under therapy.

Medical researchers have investigated a number of methods for the surgical release of intraocular pressure. Such surgery, in its simpler form, has involved making a small, surgical incision into the anterior chamber at or near the limbus to provide means for releasing an overabundance of aqueous humor from the eye into an adjacent subconjunctival space and thus to lower the intraocular pressure. In a modification of this procedure, a hair or other wicking material is reported to have been placed in the incision to provide a continuous passageway for excess fluid to be discharged from the eye. Other researchers have implanted small tubes that extend through the eye wall at the limbus or scleral-corneal junction for the purpose of providing a channel through which aqueous humor can escape.

Such surgical procedures, although still used to some extent, are far from adequate. Healing of the subconjunctival drainage space frequently results in scarring, rendering the space non-absorbent of aqueous humor. When this occurs, no liquid flow through the eye wall occurs, and the intraocular pressure may hence rise to dangerous levels. An excellent account of the history of glaucoma surgery is found in Bick, "Use of Tantalum for Ocular Drainage", *Archives of Ophthalmology*, Vol. 42: 373-388(1949).

In a recent device, the exterior end of a tube extending through the wall of the eye is provided with a pressure relief valve in the form of small slits made through the wall of the tube at its end. Reference is made to Krupin, T., et al, "Valve Implants in Filtering Surgery", *Am. J. Ophthmol.*, Vol. 81: 232-235 (1976). It is reported that fairly close control over the pressure needed to open the valve may be obtained. If the exterior or distal end of the tube is inserted beneath a flap of conjunctiva or the like, of course, the valved tube is subject to the same drawbacks as the other tubes described above. Glaucoma surgeons have discovered that when surgery fails it is usually because the "bleb", the subconjunctival drainage space created by the surgeon, has become fibrosed, causing it to shrink and become nonabsorbing.

One device that has been somewhat successful in maintaining the fluid absorbency of the bleb during the healing process was described by Molteno in 1969. Molteno, "New Implant for Drainage in Glaucoma", *British Journal of Opthalmology*, Vol. 53: 161 (1969). Molteno described a device made from a "stellon" brand acrylic monomer. The device consisted of two parts--a flat plate fashioned to conform to the sclera and a gutter incorporated at the point where a drainage tube met the plate to assure an even spread of drainage into the bleb. In 1979, Molteno disclosed a new device that had a biconcave base plate and a long silicone tube, which served the same function as the first device. Reference is made to Chapter 11 of Glaucoma Surgery by Luntz, M. H., Harrison, R. and Schenker, H. I. (1984) for a description of this device.

The drainage of fluid into spaces of the eye has been unsuccessful largely due to the problem of bleb formation. N. T. Mascati describes a different method of drainage in "A New Surgical Approach for the Control of a Class of Glaucomas", *International Surgery*, Vol. 47: 10-15 (1967). Dr. Mascati tried inserting one end of a drainage tube into the anterior chamber of an eye and the other end of the tube into the nasolacrimal duct. This procedure met with only limited success, and is not currently employed due, presumably, to problems in ocular pressure control, infections and related complications. Because the Mascati device had no means for controlling liquid flow such as a pressure relief valve there was no way (1) to prevent collapse of the anterior chamber of the eye and (2) to prevent reflux of fluid from the nasolacrimal drainage system into the anterior chamber of the eye during sneezing or nose-blowing.

BRIEF DESCRIPTION OF THE INVENTION

The invention provides a device and method for relieving high intraocular pressures associated with glaucoma. The device includes a flexible tube having one end extendable into the anterior chamber of the eye and having its other end in communication with the lacrimal drainage system of the eye. One-way valve means are provided within the tube to restrain liquid flow within the tube to a direction toward the lacrimal drainage system. Since the lacrimal drainage system is lined with epithelial cells and is a natural passageway for fluid flow, the scarring from fibrous tissue usually associated with draining is avoided. The one-way valve means also prevents back flow of fluids from the lacrimal drainage system into the eye, thus avoiding ascension of infection into the eye. One embodiment of the ocular device has filter means carried by the tube for restraining particles from passing therethrough toward the anterior chamber of the eye to further protect the eye from infection.

The method comprises the steps of inserting the one end of the tube into the anterior chamber of the eye, allowing aqueous humor to escape into the tube, and attaching the other tube end to the eye so that fluid will drain into the lacrimal drainage system. The outlet end of the tube may be inserted into the canniculi, conjunctival cul-de-sac, lacrimal sac, lacrimal duct, lacrimal passage, or nasal passage to allow fluid flow outwardly from the tube into the passages of the nasolacrimal system.

Another embodiment of the invention desirably employs a pair of one-way valves within the tube. Both one-way valves permit fluid flow only from the anterior chamber into the lacrimal drainage system. One one-way valve desirably is positioned at or near the tube and (inlet end) that will be placed into the anterior chamber. The other one-way valve desirably is positioned at or near the tube end (outlet end) inserted into the lacrimal drainage system.

DETAILED DESCRIPTION OF THE INVENTION

Figure 1:
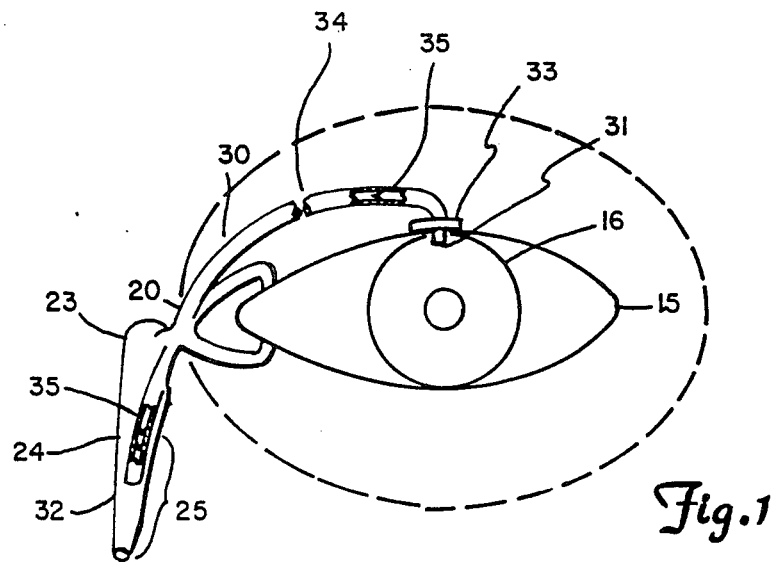
FIG. 1 is a front view of an eye showing a nasolacrimal drainage system and the device of this invention.

FIG. 1 shows somewhat schematically the front of a human eye and the lacrimal drainage system. The lacrimal gland (not shown) continuously supplies the eye with lacrimal fluid or tears. The lacrimal fluid washes across the conjunctiva (11) and the cornea (16). Excess lacrimal fluid not retained by the eye is commonly drained to the nasal passages, the inferior nasal meatus (not shown) in particular. At times the excess fluid is drained through a network of passages that commences with the puncta that appears as a small papilla adjacent the inner canthus or the inner corner of the eye. The fluid is collected in the lacrimal sac (23) by a number of canaliculi (20) connecting the puncta to the sac. The canaliculi run inferiorly then medially to the lacrimal sac. The sac (23) is then drained through its extension, the nasolacrimal duct (24) which passes into the inferior nasal meatus for this purpose. This network of passages is referred to herein as the lacrimal drainage system (25).

A tube (30) has an inlet end portion (31) that is shaped to be inserted through a small incision made in the wall of the eye so that the end (31) is positioned in the interior of the eye, preferably in the anterior chamber. The other outlet end (32) of the tube is shaped to be inserted through a small incision made in a portion of the lacrimal drainage system to be positioned therein. The tube (30), desirably is on the order of about 1 to about 8 cm long and about 0.4 to about 1.5 mm in outer diameter. The end portions may be of a comparatively rigid material such as polymethylmethacrylate or of a metal such as gold or other biologically acceptable materials, and the ends may be joined together by a more flexible length of, e.g., silicone rubber tubing. The entire length of the tube (30), including the end portions, is preferably made of a flexible material such as silicone or polyethylene.

Figure 2:
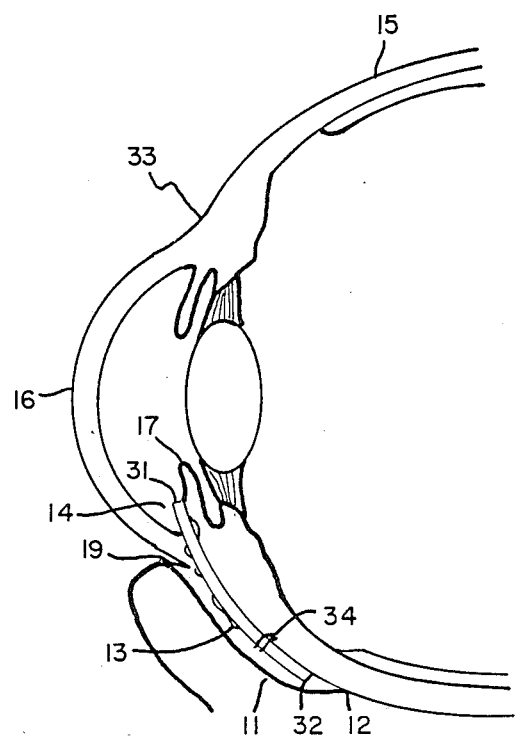
FIG. 2 is a cross-section of an eye showing a tube implanted by the method of this invention.

In FIG. 2, a cross-section of the human eye is shown that includes the device of the invention implanted in the anterior chamber. In that figure the cornea is shown as (16), the iris as (17), the lens as (18) and the limbus as (19). The inlet tube end (31) extends into the anterior chamber (14) of the eye and the outlet tube end (32) is positioned in the conjunctival cul-de-sac to allow fluid to flow from the tube into the lacrimal drainage system. The device may be secured to the sclera (15) by sutures (34) or other conventional means.

The one-way valve (35) or valves used with this invention may be of any of the various types suitable for use in the quite miniature device of the invention, and such valves often also function as pressure relief valves as well. The one-way valve employed in this method desirably is competent to prevent back flow of fluid even against increases of pressure such as those that may occur within the lacrimal drainage system when a person sneezes, blows his nose or sneezes when the nose is plugged, e.g., 500 mm Hg. The one-way valve preferably is also a pressure relief valve that is adapted to open when the pressure in the eye exceeds the pressure within the tube by a pre-set threshold pressure, e.g. by about 8–10 mm Hg. The pressure within the tube will be maintained at or near atmospheric pressure (about 760 mm Hg). In this way, the valve prevents collapse of the anterior chamber. The unidirectional flow of the fluid into the lacrimal drainage system prevents viruses and bacteria carried by fluids in the lacrimal drainage system from being carried upwardly into the interior of the patient's eye through the tube. The valves may be any of a variety of well known designs which need not be described in detail, but which might include by way of example well known "duck valves".

As explained above, the one-way valve (35) may function as a pressure relief valve, the edges of the valve flaps pressing against one another to restrain fluid flow until the pressure differential across the valve increases to a level sufficient to cause the flaps to separate slightly, permitting fluid to pass. Reversal of the pressure gradient, as when the patient sneezes, causes the flaps to press more tightly together, thus restricting flow in the opposite direction. When a tube having only one valve is used, the valve is positioned near the inlet end of the tube. The valve is thus more effective as a pressure relief valve, and back flow of fluid pooling within the tube is prevented. When two valves are used, it is desirable to have one valve near the inlet end and one near the outlet end of the tube.

The outlet end of the tube is desirably surgically inserted into the eye adjacent to or in the lacrimal drainage system. The tube end may be inserted in the conjunctival cul-de sac, the inferior or superior canaliculi (20), the lacrimal sac (23), the lacrimal duct (24), the nasal passage or any of the nasolacrimal passages or the nose. Fluid flows from the anterior chamber (14) of the eye through the tube (30) and into the passages of the lacrimal drainage system (25) and ultimately into the nasopharnyx where, if it has not been absorbed, it is swallowed.

Figure 3:
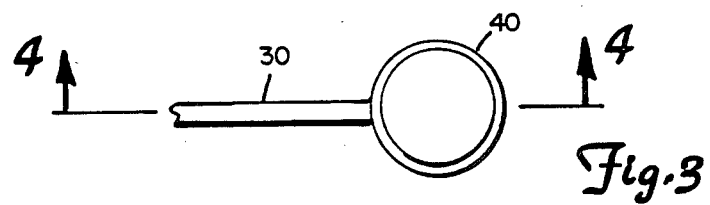
FIG. 3 is a top view of a device of this invention.
Figure 4:
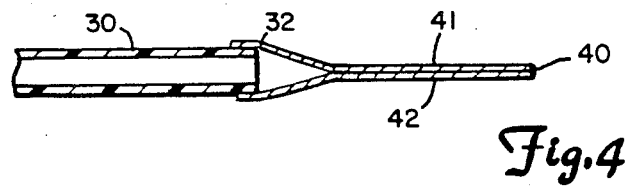
FIG. 4 is a cross-sectional view along the line A—A of the device of FIG. 3.

The ocular device shown in FIGS. 3 and 4 includes a microporous filter (40) that restrains micro-organisms and other particles having a mean diameter greater than the pore size from passing therethrough toward the anterior chamber of the eye. The filter may be of any known tyep such as a millipore filter made by the Millipore Company of Bedford, Mass. The filter desirably has a nominal pore size in the range of 0.1 micron to 10 microns and preferably has a pore size in the range of 0.1 to 0.3 micron. The filter may be carried within the tube or it may be carried at the outlet end of the tube enclosing the end. As shown in FIGS. 3 and 4 the filter may be bag-shaped and extend outwardly of the tube end. The bag-shaped filter may comprise a pair of filter sheets (41,42) joined at their peripheries to define an interior space (43) communicating with the outlet end of the tube.

One surgical technique used in practicing the method of this invention is described below. This description is included solely for illustrative purposes; the method may be practiced using any of the numerous known surgical techniques.

In the region to be operated upon, a rather large limbal based flap of conjunctiva (11) is opened with an incision of about 6 to 10 mm posterior to the limbus. Care should be taken to provide no tears or button-holing of the conjunctiva. If tears occur, they should be repaired. The episcleral tissue (13) should be cleared from the region of the limbus (19) back for a distance (i.e., 5–8 mm) and any bleeding controlled with gentle cautery. The posterior margin of the conjunctiva (11) will be lifted and Tenon's capsule (12) interrupted with combined blunt and sharp dissection until the bare sclera of the eye is visible.

Centered at the limbus (19) a partial thickness scleral flap is outlined, the flap desirably measuring 4–5 mm in width and approximately 4–6 mm in anterior-posterior length. The tube (30) should be positioned under the scleral flap and a small incision made into the anterior chamber (14) at the limbus (19). The tube end (31) will then be threaded into the anterior chamber (14) until it can be visualized through the clear cornea (16). After the tube end (31) is positioned, the limbal incision may be closed about the tube (30) and if a flange (33) is attached to the tube, it may be secured to the bed of the sclera (15) with partial thickness scleral bites and through-and-through bites through the flange (33) with a suture.

If the outlet end (32) of the tube is to be inserted into the nasolacrimal sac (23), a false channel may be created surgically in the posterior lateral wall of the sac. The tube end (32) is then threaded through that channel into the sace (23) and if desired, into the nasolacrimal duct (24). The length of the tube (30) must be sufficient to permit slippage of the tube within the sac when the eyeball rotates without dislodging the tube.

If the outlet end of the tube (32) is to be inserted into the canaliculi (20) it will desirably be threaded through the backside of the eyelid and then into the posterior wall of the canaliculus. The outlet end of the tube (32) may be attached to the eye so that it is positioned in the conjunctival cul-de-sac adjacent the lacrimal drainage system.

After the outlet tube end (32) is inserted into the nasolacrimal system (25), it is fixed to the surface of the sclera (15) under the conjunctiva (11) in the episcleral space. The tube (30) may be fixed to the eye using any well known surgical method such as sutures or scleral tunnels (34).

While a preferred embodiment of the present invention has been described, it should be understood that various changes, adaptations and modifications may be made therein without departing from the spirit of the invention and the scope of the appended claims.

What is claimed is:

1. A method for treating glaucoma in an eye having an anterior chamber and an associated lacrimal drainage system, comprising the steps of providing a tube having inlet and outlet ends and a one-way valve therebetween to allow fluid flow only toward the outlet end; surgically inserting the inlet end of the tube into an anterior chamber of the eye; and positioning and attaching the outlet end of the tube in the conjunctival cul-de-sac of the eye.

2. A method for treating glaucoma in an eye having an anterior chamber and associated lacrimal drainage system, comprising the steps of providing a tube having inlet and outlet ends and a pair of oneway valves therebetween permitting fluid flow only toward the outlet end; surgically inserting the inlet end of the tube into the anterior chamber of the eye; and surgically positioning and attaching the outlet end of the tube to the eye so that fluid will flow into the lacrimal drainage system.

3. An ocular device for glaucoma treatment comprising a flexible tube having inlet and outlet ends, shaped to be inserted into the anterior chamber of an eye and the conjunctival cul-de-sac of the eye, respectively, and a one-way valve positioned within the tube between the inlet and outlet ends to allow fluid flow only toward the outlet end.

4. The device of claim 3 wherein the one-way valve is positioned proximal to the inlet end of the tube.

5. An ocular device for glaucoma treatment comprising a flexible tube having inlet and outlet ends, shaped to be inserted into the anterior chamber and the lacrimal drainage system of an eye, respectively, and at least two one-way valves positioned within the tube between the inlet and outlet end to allow fluid flow only toward the outlet end.

6. The device of claim 5 wherein one one-way valve is positioned proximal to the inlet end of the tube and another one-way valve is positioned proximal to the outlet end of the tube.

7. An ocular device fo glaucoma treatment comprising a tube having inlet and outlet ends shaped to be inserted into the anterior chamber and the lacrimal drainage system of the eye, respectively; a one-way valve positioned within the tube between the inlet and outlet ends to allow fluid flow only toward the outlet end; and a microporous filter carried by the tube to restrain particles greater than the pore size from passing therethrough toward the inlet end.

8. The device of claim 7 wherein the filter is bag-shaped and encloses the outlet tube end, the filter extending outwardly of the tube beyond said outlet end and defining a space between two inner walls communicating with the outlet end.

9. The device of claim 8 in which the filter comprises a pair of filter sheets joined at their peripheries to define an interior space communicating with the outlet tube end.

* * * * *

UNITED STATES PATENT AND TRADEMARK OFFICE
CERTIFICATE OF CORRECTION

PATENT NO. : 4,886,488
DATED : December 12, 1989
INVENTOR(S) : THOMAS C. WHITE

It is certified that error appears in the above—identified patent and that said Letters Patent is hereby corrected as shown below:

On the title page, replace "Glaucoma Drainage the Lacrimal System and Method" with --Glaucoma Drainage in the Lacrimal System-- .

In the Abstract, line 17, replace "valve" with --valves-- .

In Column 1, line 23, replace "optica" with --optic--.

In Column 1, lines 26-27, replace "aministration" with --administration-- .

e. In Column 1, line 34, replace "simpler" with --simplest-- .

In Column 4, line 10, replace "500" with --50-- .
In Column 4, line 57, replace "tyep" with --type-- .

Signed and Sealed this

Second Day of April, 1991

Attest:

HARRY F. MANBECK, JR.

*Attesting Officer*       *Commissioner of Patents and Trademarks*